United States Patent [19]

Chamberlin, Sr.

[11] Plant 5,140

[45] Nov. 15, 1983

[54] PEACH TREE 'AUGUST SUN'

[75] Inventor: Thomas O. Chamberlin, Sr., Visalia, Calif.

[73] Assignee: H. P. Metzler & Sons, Inc., Del Rey, Calif.

[21] Appl. No.: 324,256

[22] Filed: Nov. 23, 1981

[51] Int. Cl.[3] ..... A01H 5/00

[52] U.S. Cl. ..... Plt./43

[58] Field of Search ..... Plt./43

*Primary Examiner*—James R. Feyrer

*Attorney, Agent, or Firm*—Huebner & Worrel

[57] ABSTRACT

A peach tree, denominated "August Sun", producing freestone fruit having a dark red color with bright yellow, very crisp flesh and skin tenacious to the flesh ripening August 18, to August 24.

1 Drawing Figure

BACKGROUND OF THE VARIETY

The present invention relates to a new and distinct variety of peach tree, denominated "August Sun", broadly characterized by its freestone fruit of dark red color and more particularly to such a peach tree wherein the flesh of the fruit is very crisp and of a bright yellow color having a bright red ring bounding the pit cavity and in which the pit completely fills the pit cavity with a skin which is tenacious to the flesh and ripening from August 18 to August 24 in the San Joaquin Valley of California.

The commercial market for tree fruit and particularly peaches slackens as the season reaches its latter stages. During this period, those varieties which are of high color and are resistent to damage by handling and shipping are the only ones of any substantial commercial value. The patented O'Henry peach tree (U.S. Plant Pat. No. 2,964) produces fruit having good qualities in these respects and ripening about August 6. The peach tree of the present invention is distinct in that it produces fruit of very high color, which is quite resistent to damage from handling and shipping and which ripens from August 18 to about August 24 to achieve excellent market acceptance after the harvest of the O'Henry peach.

ORIGIN AND ASEXUAL REPRODUCTION OF THE NEW VARIETY

The new variety of peach tree of the present invention was discovered by myself in 1976 and is a newly found seedling of the patented O'Henry peach tree. Seeds of the O'Henry peach tree were planted in a plot in the nursery of H. P. Metzler & Sons, Inc. at 5286 So. Del Rey Avenue, Del Rey, Calif. 93616 in 1973 and 1974. The first fruit of the present variety was observed in August, 1976 and its distinctive characteristics discovered at that time. The present variety was asexually propagated under my direction at H. P. Metzler & Sons, Inc. in 1976 and 1977 by grafting several seedlings with buds of the instant variety and planting the seedlings in a test plot on Ranch No. 18 of H. P. Metzler & Sons, Inc. at Del Rey, Calif. In 1978, 150 seedlings were budded to the new variety and planted in the same test plot at Del Rey, Calif. The seedlings of the new variety and the parent tree were observed over several growing seasons and the fruit and tree characteristics resulting from such asexual reproduction proved to be identical to those of the original seedling of the new variety.

SUMMARY OF THE NEW VARIETY

The instant variety of peach tree is characterized by its full freestone fruit having a dark red color with bright yellow very crisp flesh, a pit cavity bounded by a bright red ring wherein the pit completely fills the cavity, a skin which is tenacious to the flesh and ripening from August 18 to August 24.

BRIEF DESCRIPTION OF THE DRAWING

The accompanying drawing is a color photograph of five mature fruit of the variety of the present invention, one positioned to show the stem end, a second positioned to show the side, a third positioned to show the apex, a fourth sliced along the suture plane with the pit left in place and a fifth sliced along the suture plane with the pit removed to expose the pit cavity. A representative twig is also shown in the photograph with characteristic leaves.

DETAILED DESCRIPTION

Referring more specifically to the pomological details of this new and distinct variety of peach tree, the following characteristics were observed under the ecological conditions prevailing at the nursery of H. P. Metzler & Sons, Inc. at Del Rey, Fresno County, Calif. and is an outlined description thereof. All major color code plate identifications are by reference to the Color Name Chart of the Inter-Society Color Council, National Bureau of Standards.

TREE

Size: Normal.

Figure: Normal, subject to variation by pruning.

Productivity: Good.

Regularity of bearing: Bears very well every year.

Trunk: Normal diameter in relation to length; surface characteristics of the bark are normal with about 20–25 lenticels per square inch. Color (81-d-gy. Br.).

Branches: Normal size with normal surface; color (81-d. gy. Br.) with medium size lenticels 20–25 per square inch.

Leaves: Normal size.

*Length.*—Average length from 6 inches [15.24 CM] to 7 inches [17.78 CM].

*Width.*—$1\frac{1}{4}$ inch [3.175 CM] to $1\frac{1}{2}$ inch [3.81 CM].

*Shape.*—Lanceolate.

*Margin.*—Serrate.

*Petiole.*—About 7/16 inch [1.11125 CM] in length and 1/16 inch [0.15875 CM] thick.

*Glands.*—Not always found. If present, they are very small, and there may only be one on one side of petiole. Type: neither globose nor reniform.

*Color.*—Upper side (126 d. O1G) and under side (127 gy O1G).

Flower buds: Elongated, large light pink fluffy bud before opening.

*Diameter.*—7/16 inch [1.11125 CM].

*Length.*—11/16 inch [1.74625 CM].

Flowers:

*Date of bloom.*—March 3rd to March 8th.

*Size.*—Each petal $\frac{3}{4}$ inch [1.905 CM] in length when open and $\frac{3}{4}$ inch [1.905 CM] in width.

*Color.*—Light pink (4-1-pink).

*Number of pistils and stamen.*—1 pistil and about 38 stamen.

FRUIT

Maturity: Reached in the San Joaquin Valley of California August 18 to August 24.

Size:

*Good uniformity.*—Diameter $2\frac{3}{4}$ inches [6.985 CM] to $3\frac{1}{2}$ inches [8.89 CM]. Transverse dimension in suture plane 3 inches [7.62 CM]. Transverse dimension at right angles to suture plane about 3 inches [7.62 CM].

Form: Uniform and symmetrical.

*Suture.*—Extending from base to apex about 5 inches [12.7 CM].

*Ventril surface.*—Rounded to slightly flat.

*Stem cavity.*—Rounded and $\frac{3}{4}$ inch [1.905 CM] in depth, 1 inch [2.54 CM] in diameter.

*Apex.*—Rounded to slightly flat.

*Base.*—Wide and slightly flat.

*Pistil point.*—Slightly depressed.

Stem:

*Size.*—Length $\frac{5}{8}$ inch [1.5875 CM] and Caliper 3/16 inch [0.47625 CM].

Skin:

*Thickness.*—About 1/64 inch [0.0396875 CM].

*Texture.*—Smooth, tough and tenacious to flesh.

*Tendency to crack.*—None.

*Pubescence.*—Light.

*Color.*—(17 V.d. Red) to (12 s. Red) with some (83 Brill y).

Flesh:

*Color.*—(83 Brill y).

*Surface of pit cavity.*—Rough.

*Color of pit cavity.*—(13 Deep Red).

*Amygdalin.*—Lacking.

*Juice.*—Good, no acid taste.

*Texture.*—Smooth and crisp.

*Fibers.*—None.

*Ripening.*—Even.

*Flavor.*—Good and crisp.

*Aroma.*—Good.

*Eating quality.*—Good flavor and crisp.

Stone:

*Type.*—Freestone.

*Fibers.*—None.

*Size.*—$1\frac{3}{8}$ inches [3.4925 CM] in length and $1\frac{1}{8}$ inches [2.8575 CM] in width. Thickness, $\frac{3}{4}$ inch [1.905 CM].

*Form.*—Normal peach pit slightly longer than wide with sharp ridges running in longitudinal axes about 3/16 inch [0.47625 CM] in height.

*Base.*—Flat, about 5/16 inch [0.79375 CM] in diameter.

*Sides.*—Rough.

*Ridges.*—About $\frac{1}{8}$ inch [0.3175 CM] to 3/16 inch [0.47625 CM] in height.

*Color.*—(58 m. Br.).

*Splitting tendency.*—None.

Use: Fresh market, shipping.

*Keeping quality.*—Good. Fruit has been kept in storage from three to four weeks without noticeable deterioration.

*Shipping quality.*—Very good due to firm, crisp flesh and skin tenacious to flesh.

Although the new variety of peach tree possesses the described characteristics as a result of the growing conditions in Fresno County, Calif., in the Central portion of the San Joaquin Valley, it is to be understood that variations of the usual magnitude and characteristics incident to growing conditions, fertilization, pruning, pest control and other horticultural practices are to be expected.

Having thus described and illustrated my new variety of peach tree, what is claimed as new and desired to be secured by Letters Patent is:

1. A new and distinct variety of peach tree substantially as illustrated and described and which is characterized by its freestone fruit of dark red color having very crisp bright yellow flesh with a bright red ring bounding the pit cavity and with a skin which is tenacious to the flesh ripening August 18 to August 24.

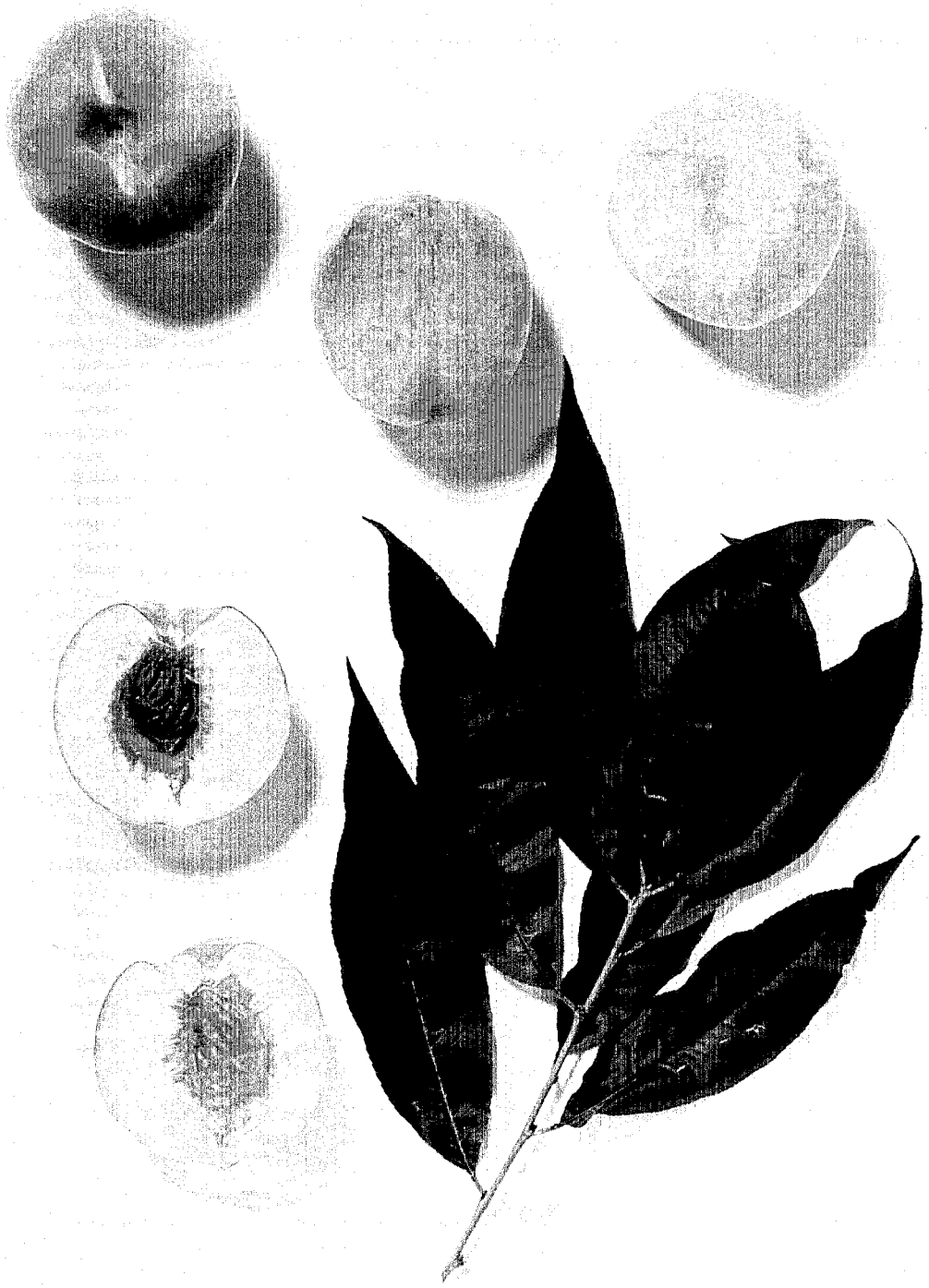

* * * * *